United States Patent
Ribeiro et al.

(10) Patent No.: US 9,939,419 B2
(45) Date of Patent: Apr. 10, 2018

(54) MODULAR SENSED ANNULAR WELL APPARATUS FOR CEMENT TESTING

(71) Applicant: Halliburton Energy Services, Inc., Houston, TX (US)

(72) Inventors: Sergio S. Ribeiro, Rio de Janeiro (BR); Flávio H. Marchesini, Rio de Janeiro (BR)

(73) Assignees: Petrobras, Rio de Janeiro (BR); Halliburton Energy Services, Inc., Houston, TX (US)

( * ) Notice: Subject to any disclaimer, the term of this patent is extended or adjusted under 35 U.S.C. 154(b) by 107 days.

(21) Appl. No.: 14/411,994

(22) PCT Filed: Oct. 30, 2013

(86) PCT No.: PCT/US2013/067601
§ 371 (c)(1),
(2) Date: Dec. 30, 2014

(87) PCT Pub. No.: WO2015/065396
PCT Pub. Date: May 7, 2015

(65) Prior Publication Data
US 2016/0274078 A1    Sep. 22, 2016

(51) Int. Cl.
*G01N 33/38* (2006.01)
*E21B 47/00* (2012.01)
(Continued)

(52) U.S. Cl.
CPC ....... *G01N 33/383* (2013.01); *E21B 47/0005* (2013.01); *E21B 47/1025* (2013.01);
(Continued)

(58) Field of Classification Search
CPC .. E21B 47/0005; E21B 47/1025; E21B 33/14; G01N 33/383; G01N 15/08; G01N 2015/0813
(Continued)

(56) References Cited

U.S. PATENT DOCUMENTS 3,974,679 A * 8/1976 Nasser ...................... G01N 3/10
73/803
2004/0221644 A1   11/2004 Go Boncan et al.
(Continued)

FOREIGN PATENT DOCUMENTS

CN    2677612 Y    2/2005
CN    202330168 U    7/2012
(Continued)

OTHER PUBLICATIONS

Authorized Officer Chan Yoon Hwang, PCT International Search Report and Written Opinion of the International Searching Authority, PCT/US2013/067601, Jul. 24, 2014, 13 pages.
(Continued)

*Primary Examiner* — Helen Kwok
*Assistant Examiner* — Nashmiya Fayyaz
(74) *Attorney, Agent, or Firm* — McDermott Will & Emery LLP

(57) ABSTRACT

In some implementations, a cement testing system includes an upper end module and a lower end module. Casing-emulating tubing couples to the upper end module and to the lower end module and emulates a wellbore casing. A plurality of intermediate well-wall-emulating modules is configured to couple end-to-end and to couple to the upper end module and the lower end module to form an annulus around the casing emulating tubing. Each of the plurality of intermediate well-wall emulating modules is configured to emulate one or more characteristics of a well wall.

17 Claims, 14 Drawing Sheets

(51) Int. Cl.
*E21B 47/10* (2012.01)
*G01N 15/08* (2006.01)
*E21B 33/14* (2006.01)

(52) U.S. Cl.
CPC .............. *G01N 15/08* (2013.01); *E21B 33/14* (2013.01); *G01N 2015/0813* (2013.01)

(58) Field of Classification Search
USPC .................................................. 73/803, 856
See application file for complete search history.

(56) References Cited

U.S. PATENT DOCUMENTS

| 2005/0152432 | A1 | 7/2005 | Hakimuddin | |
| 2006/0225523 | A1* | 10/2006 | Reddy | G01N 11/08 73/865.6 |
| 2008/0178683 | A1* | 7/2008 | Heathman | G01N 3/24 73/803 |
| 2009/0084189 | A1* | 4/2009 | McMechan | G01N 3/12 73/803 |
| 2011/0061525 | A1 | 3/2011 | Gray et al. | |
| 2011/0094295 | A1* | 4/2011 | Meadows | G01N 3/08 73/38 |
| 2013/0228019 | A1 | 9/2013 | Meadows et al. | |
| 2014/0174192 | A1* | 6/2014 | Shine, Jr. | G01N 33/383 73/803 |

FOREIGN PATENT DOCUMENTS

| WO | WO-2007/020435 A1 | 2/2007 |
| WO | WO-2012/049620 A1 | 4/2012 |
| WO | WO-2013/107789 A1 | 7/2013 |

OTHER PUBLICATIONS

De Miranda et al., "Dinâmica de Substituição de Fluidos em Poços de Petróleo", published in 2006, 8 pages.
De Souza Mendes et al., "Liquid-Liquid Displacement Flows in an Annular Space Including Viscoplastic Effects", published in 2008, 3 pages.
Dutra, "Deslocamento de Liquidos nao Newtonianos em Tubos Anulares Excentricos", published in 2005, 104 pages.
Marchesini, "Displacements Inside Oil Wells", Published in 2008, 36 pages.
Miranda et al., "Minimizing Fluid Contamination During Oilwell Cementing Operations", Mar. 28-30, 2007, 13 pages.
Sabins et al., "Transition Time of Cement Slurries Between the Fluid and Set States", Society of Petroleum Engineers of AIME, Dec. 1982, 8 pages.
Tehrani et al., "Flow Instabilities During Annular Displacement of One Non-Newtonian Fluid by Another", Experiments in Fluids, published in 1993, 11 pages.
Tinsley et al., "Study of Factors Causing Annular Gas Flow Following Primary Cementing", Society of Petroleum Engineers, Aug. 1980, 11 pages.
Dutra et al., "Analysis of Interface Between Newtonian and Non-Newtonian Fluids inside Annular Eccentric Tubes", ASME International Mechanical Engineering Congress and Exposition, Nov. 2004, 7 pages.
Extended European Search Report from European Application No. 13896401.0, dated Mar. 17, 2017.

* cited by examiner

MODULAR SENSED ANNULAR WELL APPARATUS FOR CEMENT TESTING

BACKGROUND

The specification relates to a cement testing system for predicting fluid invasion and migration phenomena in a cement column of a well after primary cementing. Fluid invasion and migration in cement are two well-known problems in the oil industry. While various contributing factors to the phenomena are associated with different cement and different well-zone characteristics, attempting to measure any of the various factors, particularly in combination, using an actual well is difficult and generally cost-prohibitive or not possible. Therefore, the predictive capability of the occurrence of fluid invasion and migration in zones of actual wells is very limited.

DESCRIPTION OF DRAWINGS

Like reference numbers and designations in the various drawings indicate like elements.

DETAILED DESCRIPTION

The specification relates to a cement testing system for predicting fluid invasion and migration phenomena in a cement column of a well after primary cementing. The details of one or more implementations of the subject matter of this specification are set forth in the accompanying drawings and the description below. Other features, aspects, and advantages of the subject matter will become apparent from the description, the drawings, and the claims.

Fluid invasion and migration into a cement column after primary cementing are two well-known problems in the oil industry. Much effort has been devoted to understand various factors contributing to the occurrence of these phenomena and to different ways to prevent their occurrence. For example, cement-related factors contributing to fluid invasion and migration can include fluid loss to the formation, shrinkage, compressibility, yield stress, transient rheology, elasticity, and density. Formation-related factors contributing to fluid invasion and migration can include formation behavior, permeability, and long term mechanical properties. Other cement-related and/or formation-related factors contributing to fluid invasion and migration are also considered to be within the scope of this disclosure.

The following description relates to an implementation of a Modular Arc Designed Sensed Annular Well (MADSAW) system and method measuring fluid invasion and migration phenomena in a cement column of a well after primary cementing. The MADSAW creates an annular space to simulate in the laboratory a region of an actual well and can, among other things, simultaneously take into account all of the above-mentioned cement- and/or formation-related factors to reproduce an actual well condition in a controlled environment and to provide a predictive capability of the occurrence of fluid invasion in zones of actual wells. Additionally, the MADSAW has an external tube that is reusable after cement curing, reducing waste of resources and total cost of ownership. The MADSAW can also be used to measure and study pre- and post-cement set scenarios as well as a set cement sheath once the cement cures. As an example of pre-cement set scenario, the MADSAW can be used to study the effects of fluid properties and flow behavior on the displacement efficiency of one fluid by another inside an annular space, simulating a cement placement operation. The MADSAW permits testing of new technologies in a controlled laboratory environment before transitioning the technologies to the field.

Figure 1A:
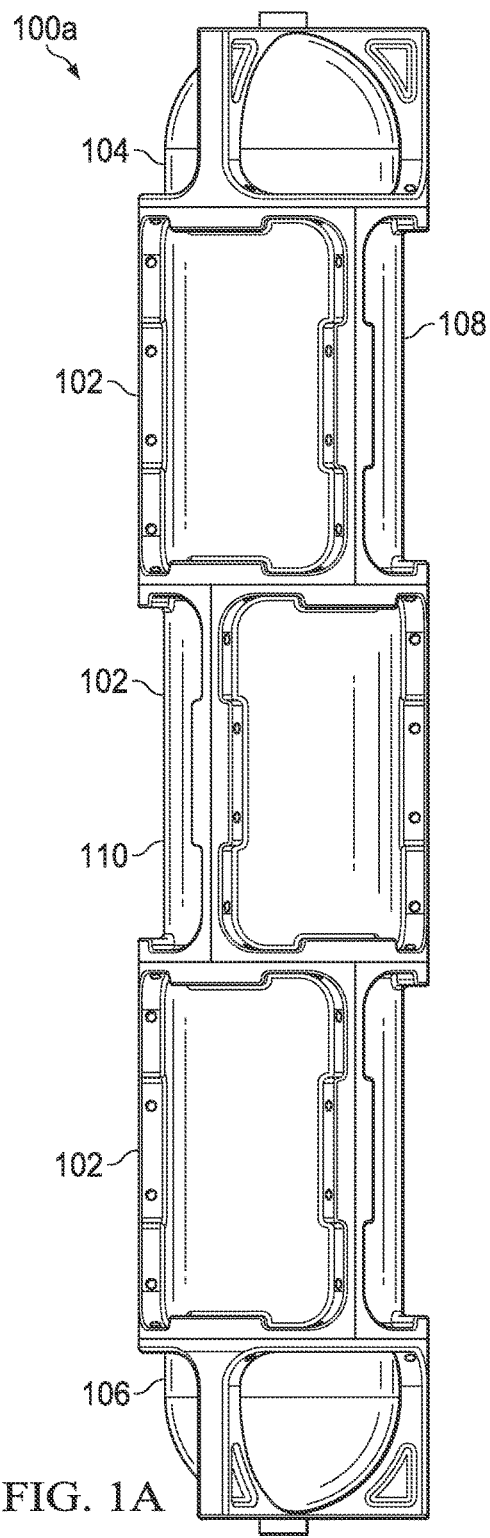
FIG. 1A is side view of an example modular are designed sensed annular well (MADSAW) system according to an implementation.

FIG. 1A is side view 100a of an example MADSAW system according to an implementation. At a high level, in some implementations, the MADSAW includes one or more intermediate well-wall emulating modules (WEMs) 102, a top module (TM) 104, and a bottom module (BM) 106. Each WEM 102 is formed from a combination of regular arc modules (RAMs) 108 and/or special arc modules (SAMs) 110. The TM 104 and BM 106 couple to an upper-end WEM 102 and to a lower-end WEM 102, respectively, and to a casing emulating tubing (not illustrated—refer to FIG. 1B) situated within the coupled WEMs 102. The coupled WEMs 102 form an emulated annular space (not illustrated—refer to FIG. 1B) around the casing emulated tubing. The TM 104 and BM 106 seal the emulated annular space.

Figure 1B:
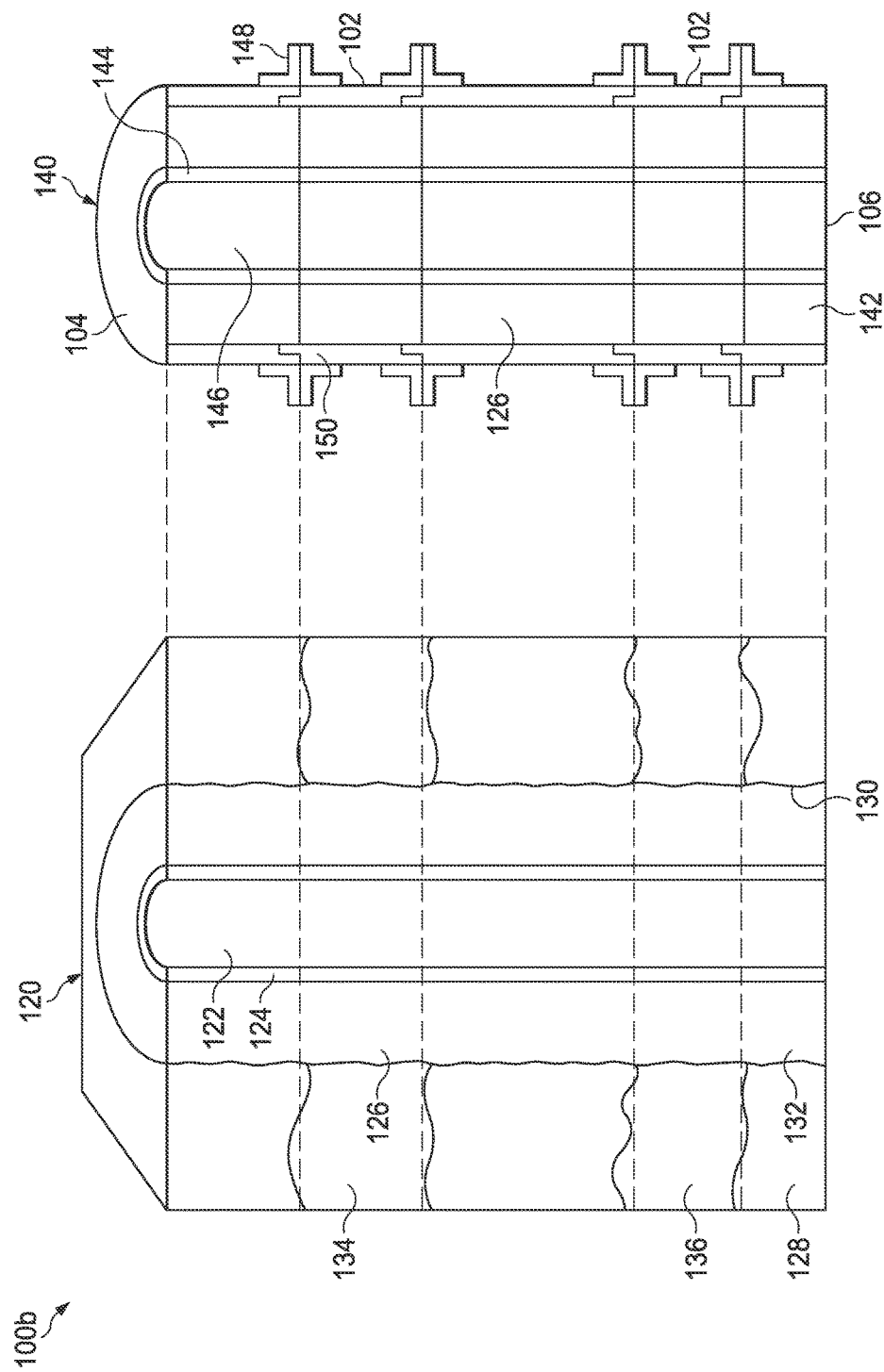
FIG. 1B is an illustration of an actual well in relation to an emulated well according to an implementation.

FIG. 1B is an illustration 100b of an actual well in relation to an emulated well according to an implementation. FIG. 1B illustrates both an actual well 120 and an emulated well 140 (e.g., using the MADSAW illustrated in FIG. 1A). An exemplary actual well 120 includes a wellbore 122, a wellbore casing 124, cement 126, and a subterranean formation 128 through which the actual well 120 is drilled comprising one or more zones. The edge of the subterranean formation 128 adjacent to the cement forms a well wall 130. The space between the well wall 130 and the outer surface of the wellbore casing 124 form an annular space 132 (here filled with cement 126). Although illustrated with a single wellbore casing 124, in some actual wells 120, multiple diameter wellbore casings 124 can be nested partially within each other forming a plurality of differently sized annular spaces 132. Each zone of the subterranean formation 128 can have different properties. For example, the illustrated permeable zone 134 can be permeable to a fluid or gas, such as water or natural gas, respectively, and the high-pressure zone 136 can subject the cement 126 at the well wall 130 of the high-pressure zone 136 to high pressures.

The emulated well 140 is illustrated using a simplified MADSAW as shown in FIG. 1A. The MADSAW creates an emulated annular space (annulus) 142 around a casing emulated tubing 144 surrounding an emulated wellbore 146 using a plurality of WEMs 102 that are assembled in such a way to reproduce the different subterranean formation 128 zones of an actual well 120, as illustrated in FIG. 1. For example, WEM 102 can be used to emulate a permeable zone corresponding to the permeable zone 134 of the illustrated actual well 120. Similarly, a WEM 102 can be used to emulate a high-pressure subterranean zone corresponding to the high-pressure zone 136 of the illustrated actual well 120. The WEMs 102 can be arranged in such a manner as to emulate different actual well zone configurations. In some implementations, similar WEMs 102 can be combined, as needed, to provide additional length to cover different subterranean formation 110 zone lengths.

As illustrated, WEMs 102 can be coupled using a combination of one or more end flanges 148 and one or more interlocking end edges 150. Any appropriate fastener (not illustrated) can be used in combination with the end flanges 148 to secure together the one or more end flanges 148 and to couple two WEMs 102. Fasteners can include screws, bolts/nuts, rivets, welds, adhesives, and/or other fasteners. The interlocking end edge 150 (at the top and bottom of each illustrated WEM 102) forms a "groove" for an interlocking end edge 150 of a second WEM 102 to fit into.

The casing emulating tubing 144 surrounding the emulated wellbore 146 forms an emulated wellbore casing corresponding to the wellbore casing 126 of the actual well 120. The emulated annular space 142 between the interior surface of the WEMs 102 and the outer surface of the casing emulating tubing 144 can hold cement 126 and/or other substances.

The MADSAW also provides an upper end module 132 and a lower end module 134 (neither illustrated in detail). The top module 132 and bottom module 134 couple to an upper-end WEM 102 and a lower-end WEM 102, respectively, and to the casing emulating tubing 144 to seal the emulated annular space 142

Figure 2A:
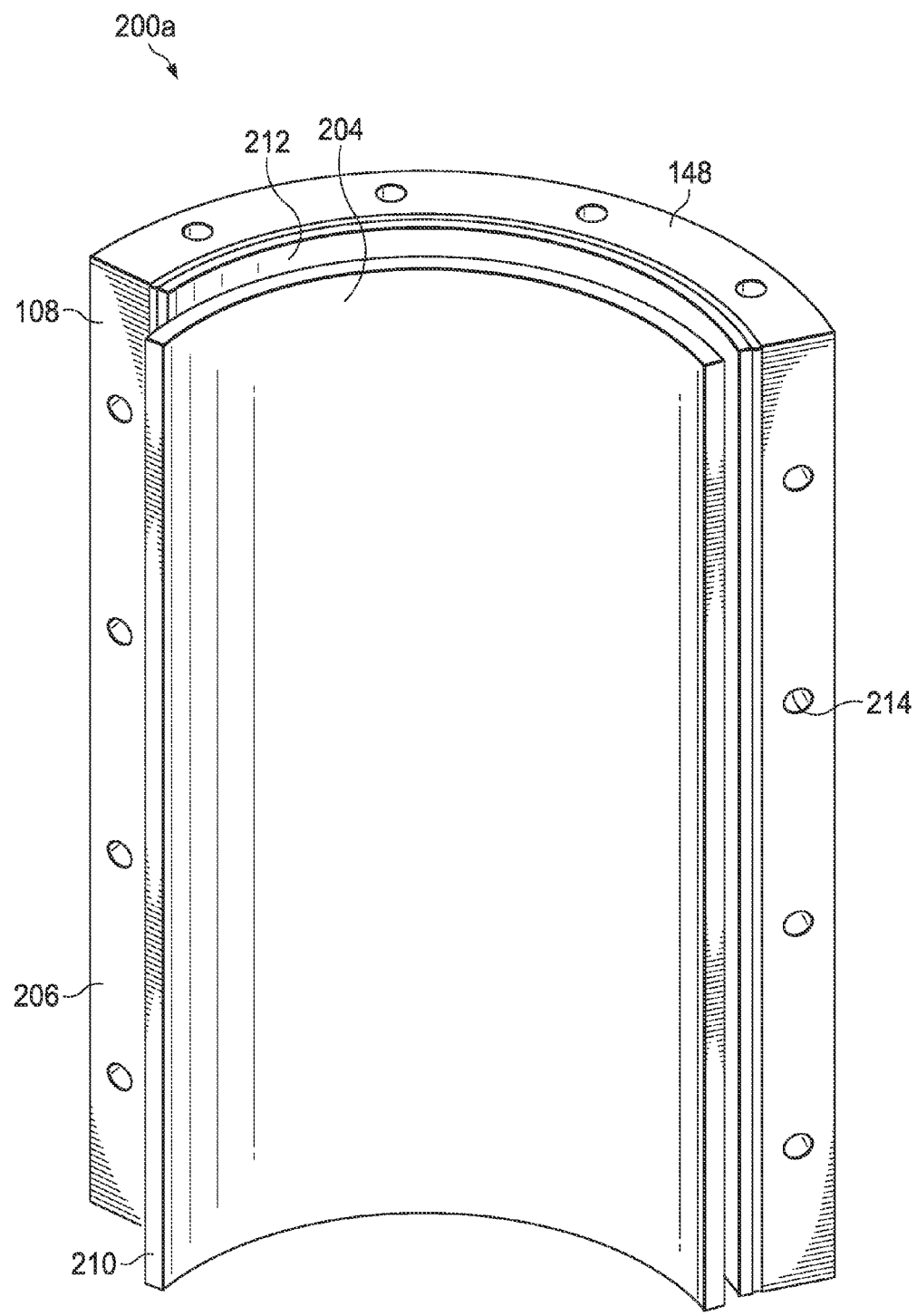
FIG. 2A is a perspective view illustrating the interior of a regular arc module (RAM) according to an implementation.
Figure 2B:
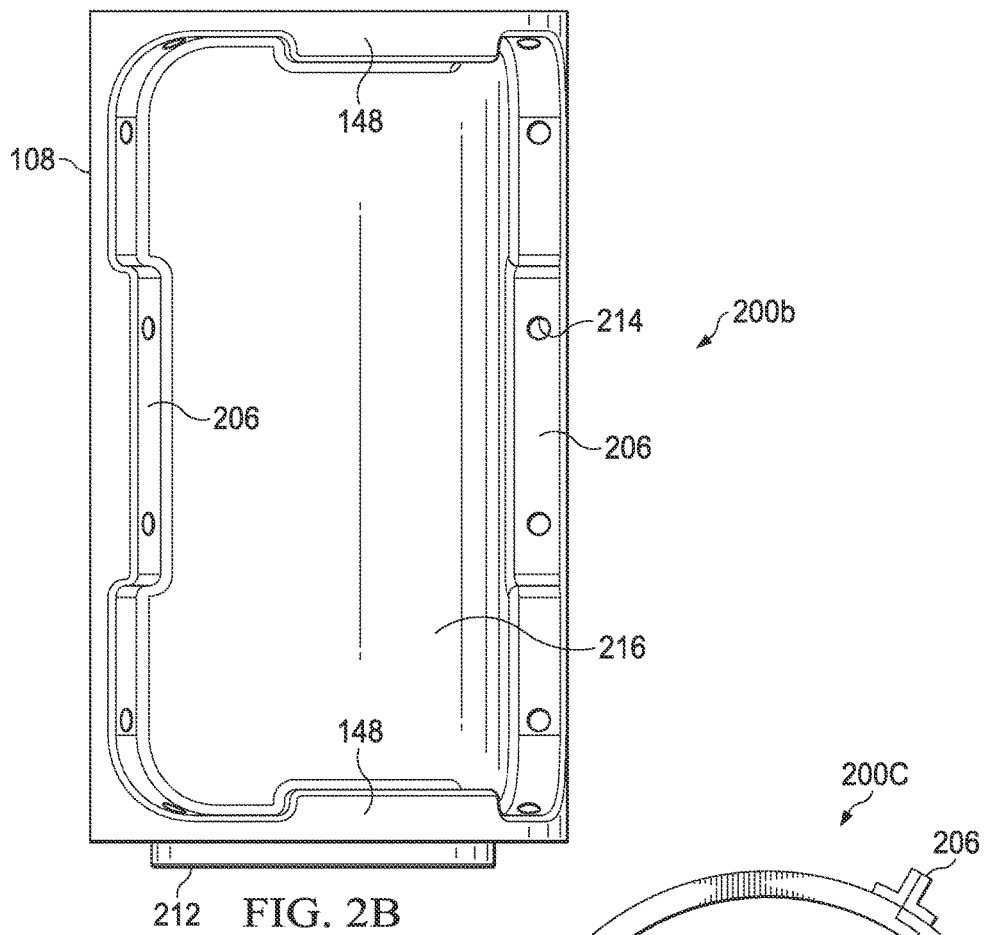
FIG. 2B is a view illustrating the exterior of a RAM according to an implementation.
Figure 2C:
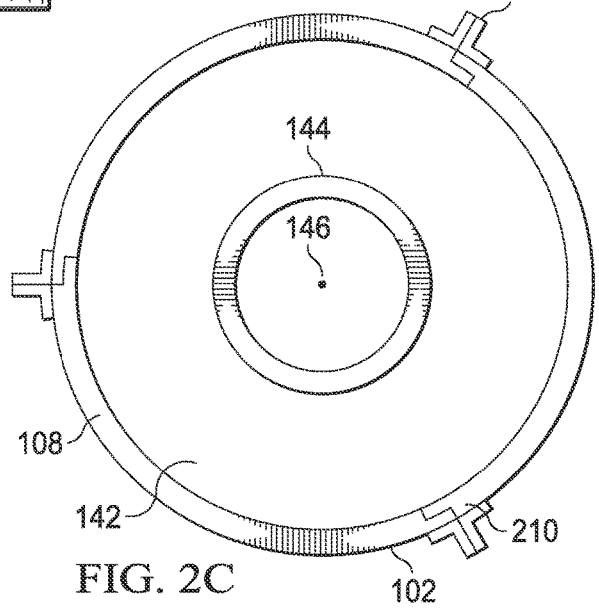
FIG. 2C is an intermediate axial cross-section of a plurality of RAMs used to form an intermediate well-wall emulating module (WEM) and an annulus around an emulated wellbore casing according to an implementation.

FIGS. 2A-2C illustrate views 200a-200c of regular arc modules (RAMs) used to form a WEM 102 as illustrated in FIG. 1. FIG. 2A is a perspective view 200a of the interior of a RAM 108 according to an implementation. RAM 108 is configured with one or more side flanges 206, one or more end flanges 148 (the "bottom" end flange 148 is not shown), interlocking side edges 210, and interlocking end edges 212. In some implementations, the side flanges 206 extend axially the length of the RAM 108. In other implementations, the side flanges can be configured to form one or more separated side flanges 206 axially along the length of the RAM 108. The interlocking side edges 210 form a lip/groove along the sides of the RAM 108 which interlock with a corresponding groove/lip of another RAM 108. In some implementations, the interlocking side edges 210 can be coupled with a sealing material (not illustrated) to form a hermetic seal with an interlocking side edge 210 of another RAM 108. For example, the sealing material can be rubber, plastic, silicone, and/or other sealing material.

Once interlocking side edges 210 of two RAMs 108 are interlocked, the corresponding side flanges 206 can be joined together with a fastener to secure the RAMs 108. For example, the illustrated side flanges 206 are shown configured with plurality of fastener holes 214 passing through the side flanges 206 that can be used with bolt and nut type fasteners.

FIG. 2B is a view 200b illustrating the exterior of a RAM according to an implementation. As illustrated, the RAM 108 has an exterior surface 216. A particular implementation of the side flange 206, end flange 208, and interlocking end edge 212 as well as fastener holes 214 are also illustrated. Various implementations may have differently shaped side flanges 206, end flanges 148, and/or interlocking end edges 212. In some implementations, there can be more or less fastener holes and/or different structures may be used for fasteners along the side edges 206 and/or end edges 208.

FIG. 2C is an intermediate axial cross-section 200c of a plurality of RAMs 108 used to form WEM 102 and an annulus 142 around casing emulating tubing 144 according to an implementation. Each RAM 108 that couples to form the WEM 102 forms a portion of the complete perimeter of the outer edge of the annulus 142 formed around the casing emulating tubing 144. Each illustrated RAM 108 would span one-hundred and twenty degrees of the circumference of the illustrated WEM 102 forming the circular annulus 142 around the casing emulated tubing 144. In other implementations, more or less RAMs 108 can be needed to form an annulus 142 around the casing emulated tubing 144. For example, in some implementations, two RAMs 108 can be used, while in other implementations, three RAMs 108 can be used (as illustrated in the FIG. 3A). While RAM 108 has been illustrated to be circular in shape, in other implementations, RAM 108 can be of any appropriate shape. For example, RAM 108 could form a right angle and two or four RAMs 108 could be required to complete a square-shaped WEM 102 and annulus 142 around the casing emulated tubing 144. Other RAM 108 shapes are considered to also be within the scope of this disclosure.

In some implementations, RAMs 108 forming a WEM 102 can each span different portions of the perimeter of the outer edge of an annulus. For example, two RAMs 108 could each span sixty degrees of the perimeter of a circular annulus 142, while two other RAMs 108 could each span one-hundred and twenty degrees to complete the perimeter.

Figure 3A:
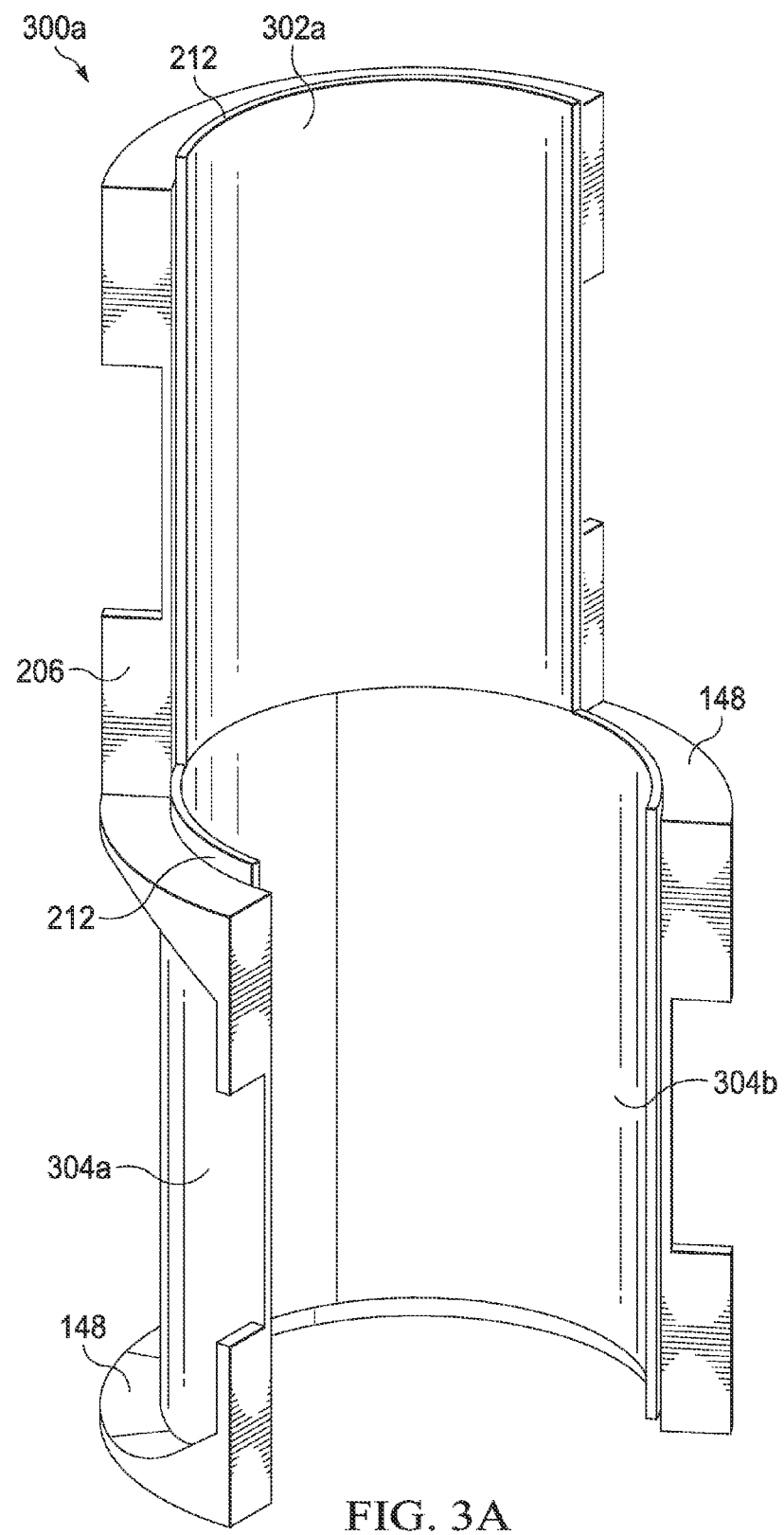
FIG. 3A is a perspective view of RAM positional relationships with respect to coupled partial WEMs according to an implementation.

FIG. 3A is a perspective view 300a of RAM 108 positional relationships with respect to coupled partial WEMs 102 according to an implementation. To avoid stress concentration points in the MADSAW, in some implementations, RAMs 108 associated with a first WEM 102 can be rotated with respect to adjacent RAMs 108 associated with a second WEM 102. For example, RAM 302a is rotated approximately sixty degrees in relation to RAMs 304a/304b so that the edges of the RAMs do not line up with edges of adjacent RAMs. Note that the side flanges 206 are illustrated with an alternate configuration as compared to that shown in FIGS. 2A-2C. Fastener holes 214 are also not illustrated.

Referring back to FIG. 2A, the end flanges 148 and an end edges 212 are used in a similar manner to that of the side flanges 206 and side edges 210, respectively, to couple a first WEM 102 to a second WEM 102. For example, the WEM 102 formed by RAMs 304a/b (and another not illustrated RAM) is coupled to the WEM 102 formed by RAM 302a (and two other not illustrated RAMs).

Figure 3B:
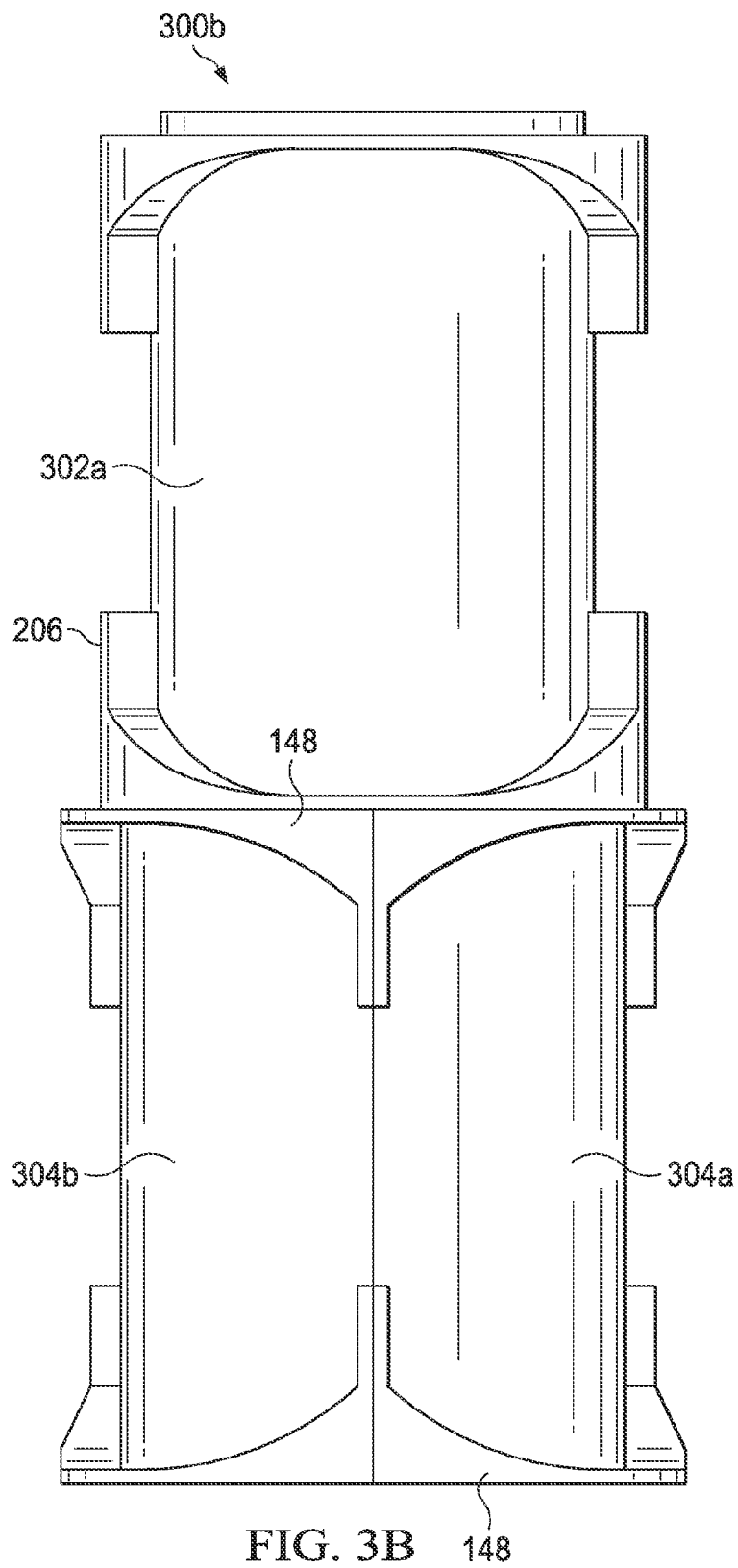
FIG. 3B is a rear view of FIG. 3A according to an implementation.

Turning now to FIG. 3B, FIG. 3B is a rear view 300b of FIG. 3A according to an implementation. Coupled alternate configurations of side flanges 206 and end flanges 148 are illustrated as discussed above with respect to FIG. 3A.

Figure 4A:
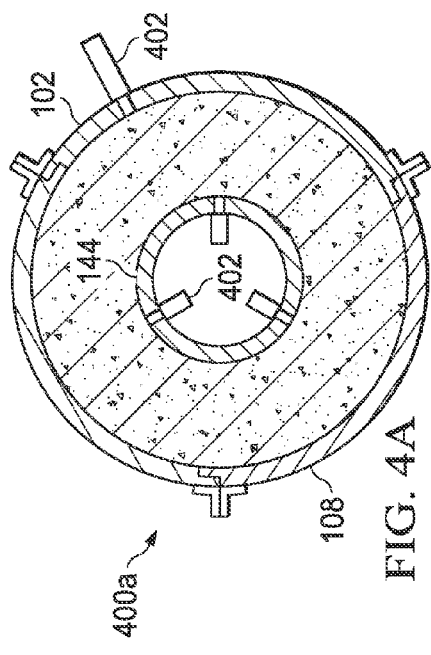
FIG. 4A illustrates a sensored intermediate axial cross-section of FIG. 2C according to an implementation.
Figure 4B:
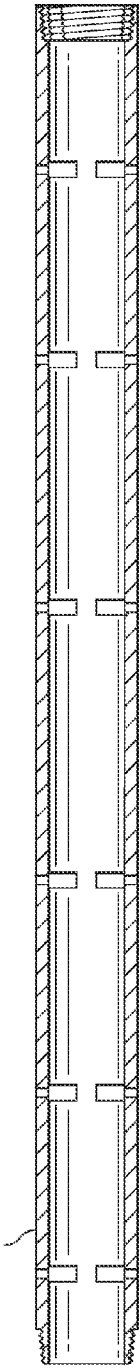
FIG. 4B is an illustration of a single piece casing emulating tubing according to an implementation
Figure 4C:
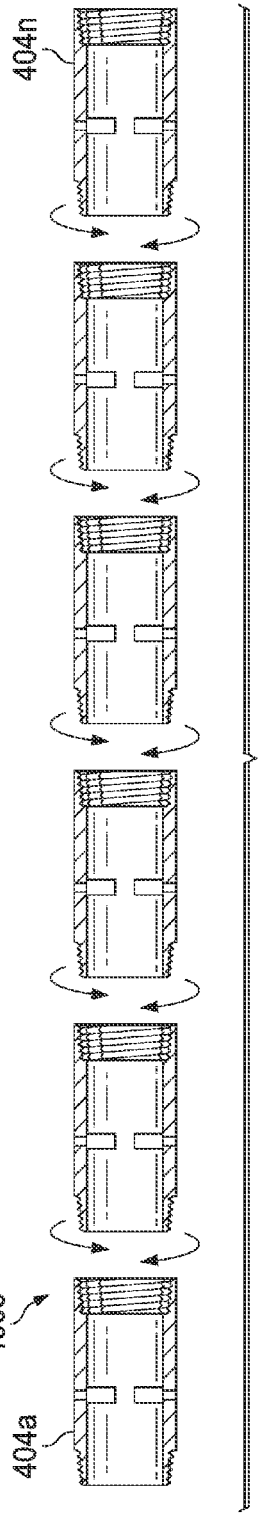
FIG. 4C is an illustration of a modular casing emulating tubing according to an implementation.

FIGS. 4A-4C illustrate views 400a-400c of a casing emulated tubing 144 and sensor placement according to an implementation. FIG. 4A illustrates a sensored intermediate axial cross-section of FIG. 2C according to an implementation. As illustrated, one or more associated RAMs 108 can be individually sensored (e.g., with sensor 402). Sensors 402 can be for temperature, pressure, strain, and/or other sensors and create a mesh of sensors through the MADSAW system. Sensors 402 monitor important physical quantities during a simulated scenario, providing insight into what is happening inside the MADSAW during testing. In some implementations, the casing emulating tubing 144 can be adapted with a sensor 402 to measure one or more characteristics of cement at the exterior of the casing emulating tubing 144.

FIG. 4B is an illustration 400b of a single piece casing emulating tubing 144a according to an implementation. Placement and/or reconfiguration of the sensor 404 within the single piece casing emulating tubing 144a can be difficult, time consuming, and/or cost prohibitive.

FIG. 4C is an illustration 400c of a modular casing emulating tubing 144 according to an implementation. In some implementations, the modular casing emulating tubing 144b is formed from a plurality of single-piece intermediate tubing modules 404a . . . 404n that couple end-to-end to define an entire length of a casing emulating tubing 144. In some implementations, fasteners can be used to couple the plurality of single-piece intermediate tubing modules 404a . . . 404n. In some implementations, each intermediate tubing module 404 has at least one threaded end to permit two intermediate tubing modules 404 to couple end-to-end. In some implementations, one or more of the intermediate tubing modules 404 can be adapted with a sensor 402 to measure one or more characteristics of cement at the exterior of the casing emulating tubing. In this configuration, sensors 402 associated with an intermediate tubing module 404 in the interior/middle of a casing emulating tubing 144b can be unscrewed and swapped out for different sensors 402 much easier than in the implementation of the single piece casing emulating tubing 144a of FIG. 4B. This modular design provides the advantage of allowing the MADSAW to have more sensors 402 placed along its length, because of relative ease of sensor 402 placement.

Special Arc Modules (SAMs) 110 (as illustrated in FIG. 1A) are RAMs 108 modified for special purpose use. The SAMs 110 share groove/edge and flange connection patterns as described above, and can be assembled in different ways with RAMs 108 to form a variety of WEM 102 configurations. In some implementations, each WEM 102 can include different combinations of RAMs 108 and/or SAMs combined to form the perimeter of a WEM 102. Several well conditions and scenarios can be reproduced individually or at the same time, depending on the assembled configuration.

Figure 5:
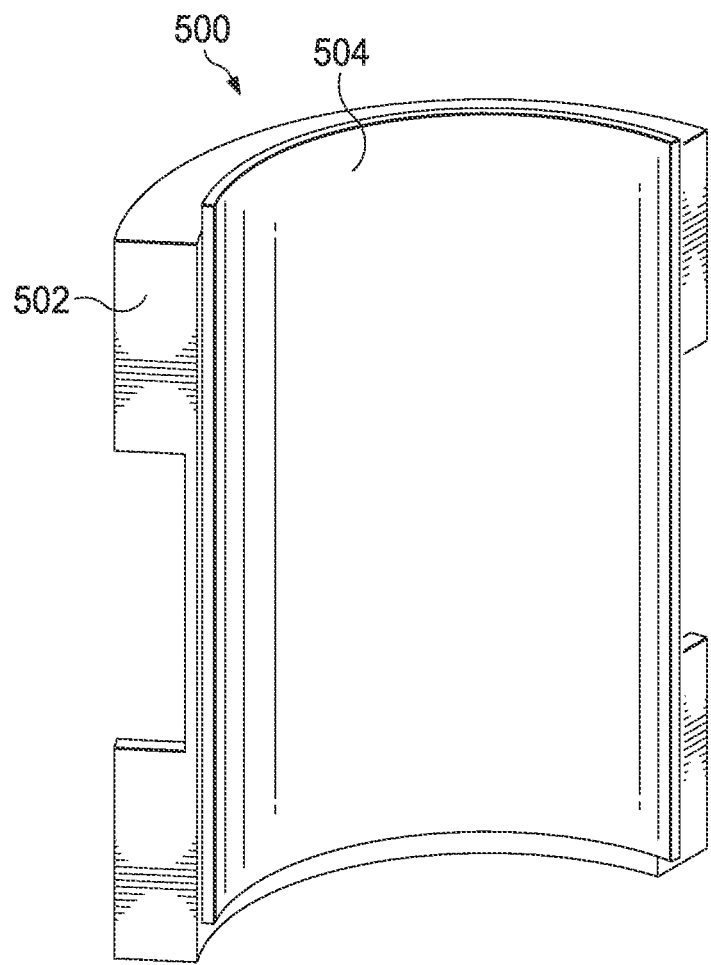
FIG. 5 is an interior view of a roughened module (RM) special arc module (SAM) according to an implementation.

FIG. 5 is an interior view 500 of a roughened module (RM) SAM 110 according to an implementation. In some implementations, the only difference between a roughened module (RM) 502 and a RAM 204 is the roughness of the internal surface 504, as illustrated in FIG. 5. For example, the roughness of the internal surface 504 of a roughened module (RM) 502 can range between 1 and 100 micrometers. In other implementations, macroscopic roughness ranging from 0.5 to 2 millimeters can be created on the internal surface 504 of a roughened module (RM) 502. The roughness of the internal surface 504 is different than a roughness produced merely as a product of manufacturing the internal surface 504 of RM 502. The roughness for the internal surface 504 is specially applied to the interior surface 504. For example, the interior surface 504 can be machined, cast, adhered to, and/or manufactured in some other manner to yield a specified roughness. The roughness modification is designed for two primary purposes: 1) investigating well-wall roughness effects on simulated physical processes in the MADSAW, and 2) to prevent the occurrence in the MADSAW of phenomena such as apparent wall slip that can be observed in well field operations.

In typical implementations, roughness of a RM 502 can be easily configured using computer-aided drafting tools to produce a mold used to produce the RM 502 consistent with a specified roughness. Additionally, sets of RMs 502 with different roughness values can be assembled to emulate a well with multiple formation structures of various roughness values. To allow for a good comparison with the use of smoothly surfaced RAMs 204, RMs 502 can be configured with the same sensors (not illustrated) that the RAMs 204 are configured with (as illustrated in FIG. 4 with sensor 402).

Figure 6C:
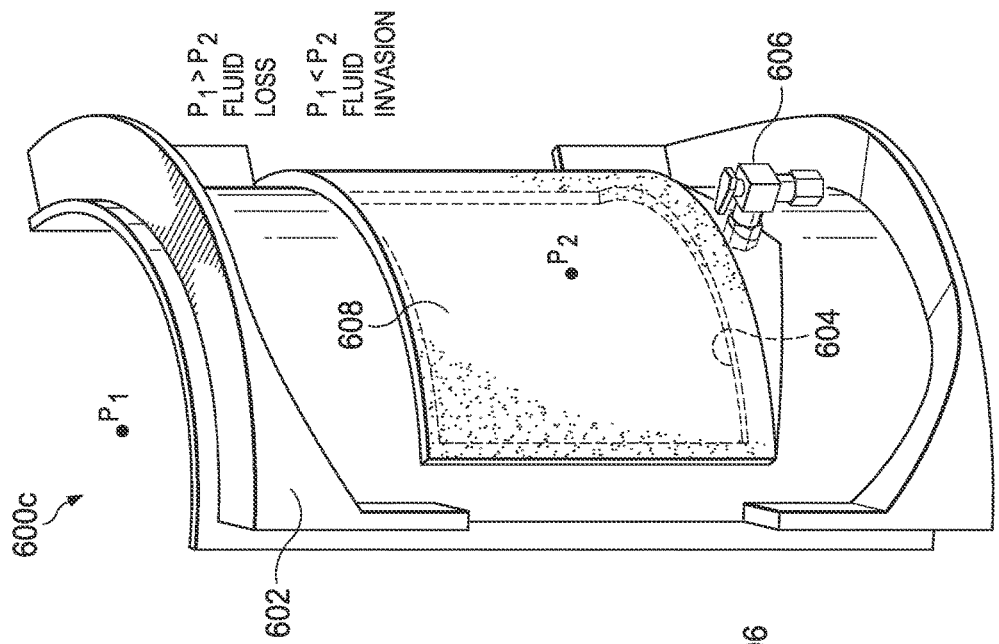
FIG. 6C is a perspective view of a FEM SAM according to an implementation.
Figure 6B:
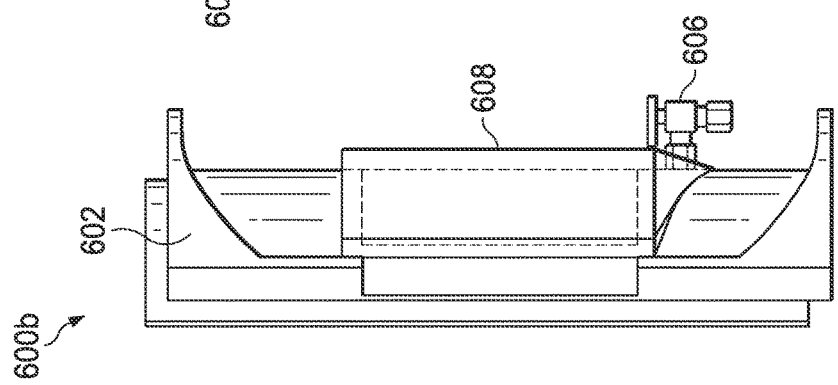
FIG. 6B is a side view of a FEM SAM according to an implementation.
Figure 6A:
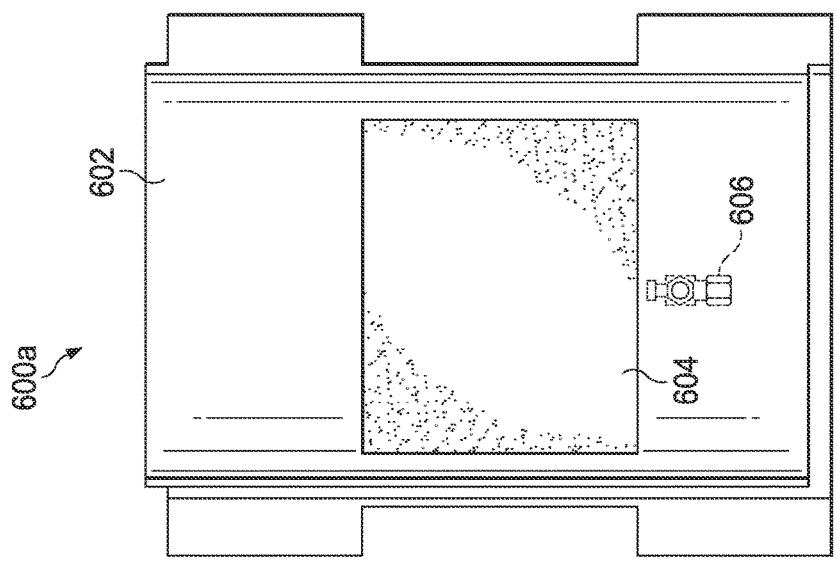
FIG. 6A is a front view of a fluid exchange module (FEM) SAM according to an implementation.

FIGS. 6A-6C illustrate views 600a-600c of a fluid exchange module (FEM) according to an implementation. In some implementations, a RAM 108 is adapted as a fluid exchange module (FEM) to include a hermetic enclosure separated from the annulus 142 by an interface material with a specified permeability to fluid or gas to emulate different permeabilities of a well-wall in, for example, a highly-permeable zone or a high-pressure gas zone. In some implementations, a two-way valve is connected to the hermetic enclosure to establish a positive, equal, or negative pressure within the hermetic enclosure. FIG. 6A is a front view 600a of a FEM SAM according to an implementation. The FEM 602 has a permeable material 604 and two-way valve 606. More than one set of FEMs 602 can be assembled in different MADSAW sections on an emulated well 140 to analyze the effect of changing the permeability between adjacent subterranean formation 128 layers. In some implementation, the permeable material 604 can be a metal mesh. In some implementations, the hermetic enclosure 608 can be made of polycarbonate or acrylic to permit visualization or from steel if the pressure $P_2$ is to exceed a tolerance threshold for the use of other materials. In some implementation, the two-way valve 606 can be automated by testing equipment to increase or decrease pressure within the hermetic enclosure 608 by allowing either the inlet or outlet of a fluid or gas.

FIG. 6B is a side-view 600b of a FEM SAM according to an implementation. FIG. 6B also illustrates the hermetic enclosure 608 surrounding the permeable material 604.

FIG. 6C is a perspective view 600c of the FEM SAM according to an implementation. As illustrated, a pressure $P_2$ can be applied inside the hermetic enclosure 608 to simulate either fluid loss or invasion depending on the magnitude of $P_2$ compared to $P_1$, the pressure inside the annulus. If $P_1>P_2$, than fluid loss can be simulated, otherwise fluid invasion can occur.

In some implementations, FEMs 602 can be configured with sensors 402 similar to those used with RAMs 108 and the casing emulated tubing 144, in addition to a flow metering device (not illustrated) connected to the two-way valve 606 to measure a fluid loss/invasion flow rate. To enhance precision with a determination of $P_2$, the two-way valve 606 can, in some implementations, be replaced by an electrical valve with pressure control.

Figure 7B:
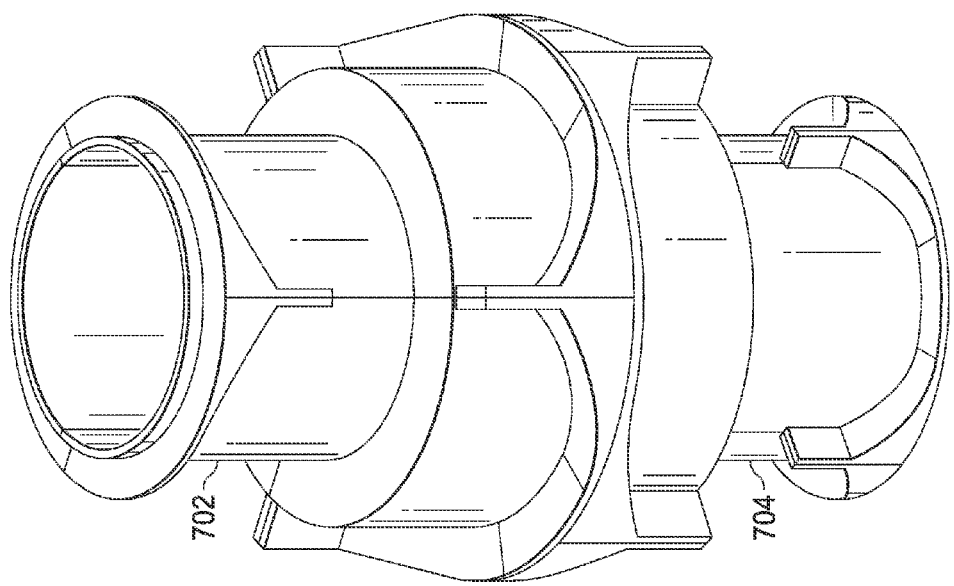
FIG. 7B is a perspective view of a coupled WM SAM and a NM SAM according to an implementation.
Figure 7A:
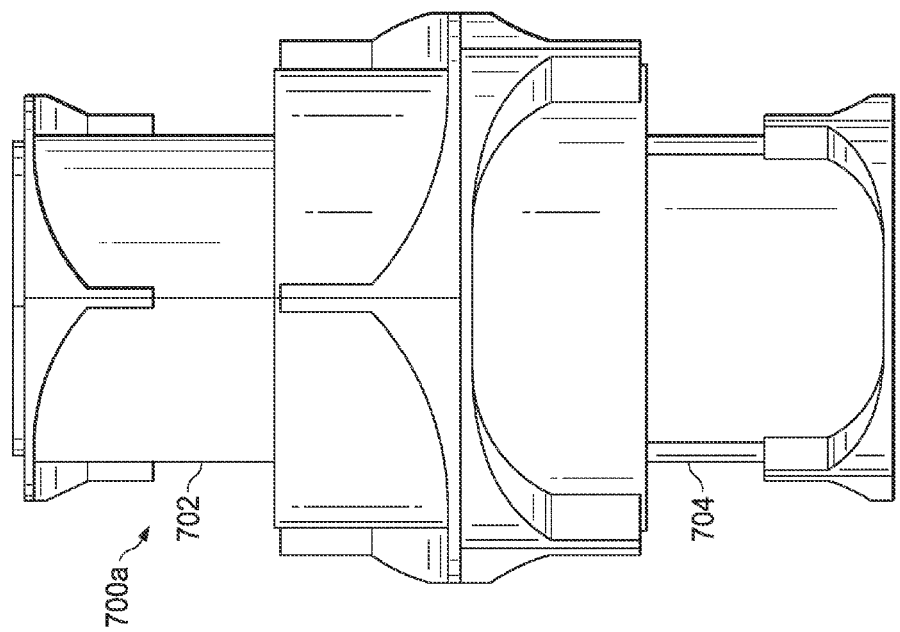
FIG. 7A is a side view of a coupled widening module (WM) SAM and a narrowing module (NM) SAM according to an implementation.
Figure 7C:
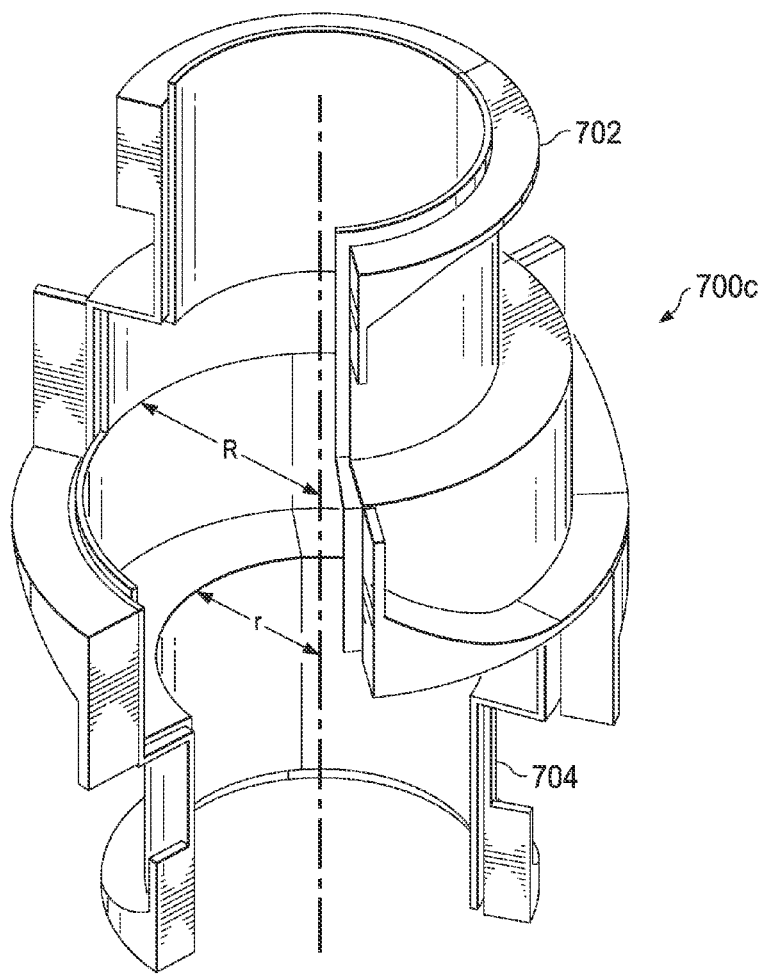
FIG. 7C is a cut-away view of a coupled WM SAM and a NM SAM according to an implementation.

FIGS. 7A-7C illustrate views 700a-700c of views of a widening module (WM) and a narrowing module (NM) according to an implementation. Abrupt radius (r→R→r) variations of the annulus can drastically change flow behavior. WMs and NMs allow observation of the influence of radius changes in experiments such as fluid loss and cement placement. Modifying RAMs 204 with a radius R instead of r allows simulation of telescopic well sections and the evaluation of behavior of different slurries flowing through an expansion and/or contraction of a well. In some implementations, WMs and NMs are configured with the same sensors (e.g., sensor 402 of FIG. 4) as RAMs 204 for gathering data.

FIG. 7A is a side view 700a of a coupled WM 702 SAM and a NM 704 SAM according to an implementation. FIG. 7B is a perspective view 700b of a coupled WM 702 SAM and a NM 704 SAM according to an implementation.

FIG. 7C is a cut-away view 700c of a coupled WM 702 SAM and a NM 704 SAM according to an implementation. An abrupt radius (r→R→r) variation as described above is illustrated.

Figure 8:
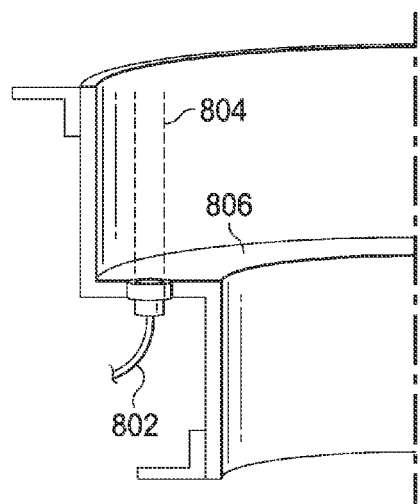
FIG. 8 is an illustration of the use of a capacitive load cell on a horizontal surface of a WM or a NM according to an implementation.

FIG. 8 is an illustration 800 of the use of a capacitive load cell on a horizontal surface of a WM 702 or a NM 704 according to an implementation. A WM 702 or a NM 704 can be configured with a capacitive load cell 802 or other sensor to measure a weight of a fluid column 804 above (or below in the case of a NM 704) a horizontal surface 806. In some implementations, other types of sensors can be substituted for, or used in conjunction with, the capacitive load cell 802 to collect data. For example, other sensors could be for temperature, pressure, and/or other data.

Figure 9A:
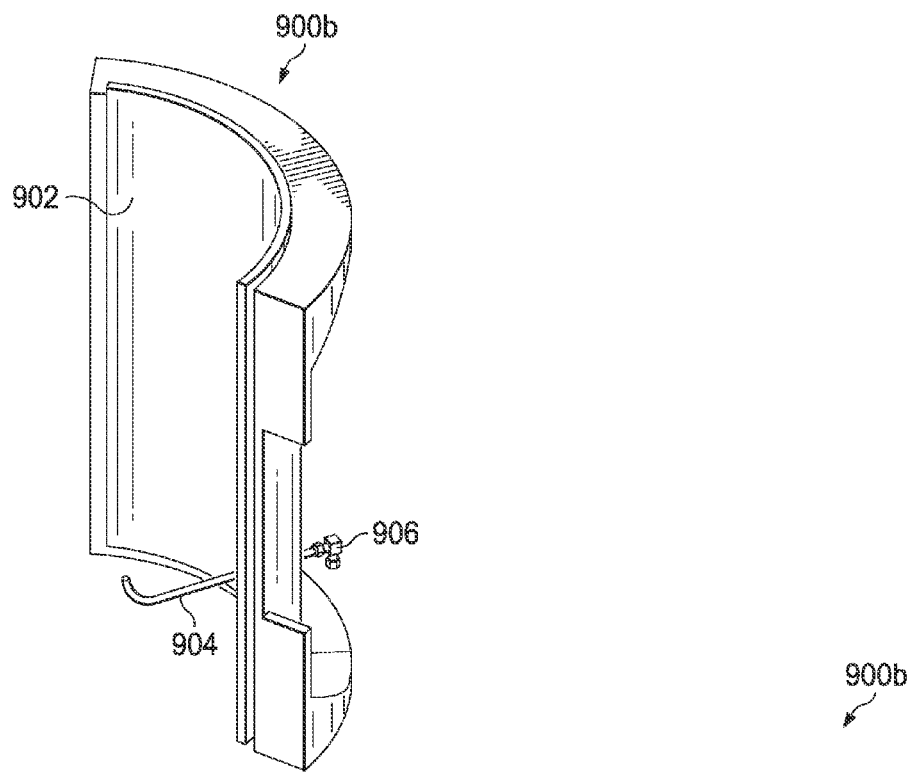
FIG. 9A is a perspective view of a fluid injection module (FIM) SAM according to an implementation.

FIG. 9A is a perspective view 900a of a fluid injection module (FIM) SAM according to an implementation. The fluid injection module (FIM) 902 is typically a RAM 108 pierced by a small pipe 904 connected to a one-way valve 906, which prevents contents within the annulus 142 from leaking through the small pipe 904. The FIM 902 is designed for investigating the injection of a gas through the small pipe 904 into a cement slurry column, allowing for a better understanding of bubble growth and bubble migration phenomena.

Figure 9B:
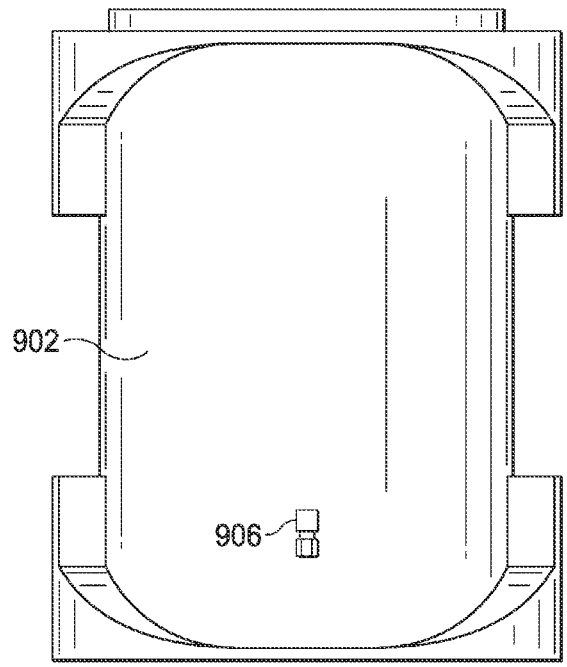
FIG. 9B is a front view of the FIM of FIG. 9A according to an implementation.

In some implementations, the FIM 902 is configured with a sensor 402 in addition to a flow sensor incorporated into the one-way valve 906. In some implementations, transparent FIMs 902 and RAMs 108 can be used together with a transparent modeling fluid if visualization is required; otherwise analysis of a cement 126 after curing can be made as a way to evaluate the bubble growth and bubble migration phenomena in each test. In some implementations, the FIM 902 can be used for the injection of other fluids besides gases. FIG. 9B is a front view 900b of FIG. 9A according to an implementation.

The bottom module (BM) and top module (TM) are SAMs designed not only to close the bottom and the top of the annulus 142, respectively, but also, when desired, to allow the addition of an eccentricity on casing emulating tubing 144 of the MADSAW. In some implementations, each of the BM and TM has an internal wireframe, in which the casing emulating tubing 144 is connected. The internal wireframe can be changed in the TM and/or BM according to a desired eccentricity of the casing emulating tubing 144 in relation to the outer diameter of the annulus 142 formed by a plurality of WEMs 102.

Typically, both the top and the bottom of the casing emulating tubing 144 are sealed to prevent entry of fluid into the casing emulating tubing 144. In some instances, however, this configuration can be changed depending on a particular application under consideration. For example, fluid can be pumped from the top of the casing emulating tubing 144 and a study performed of the fluid displacement inside the annulus 142. As will be appreciated by those of skill in the art, various modifications can be made to components of the MADSAW to accomplish desired types of testing.

Figure 10A:
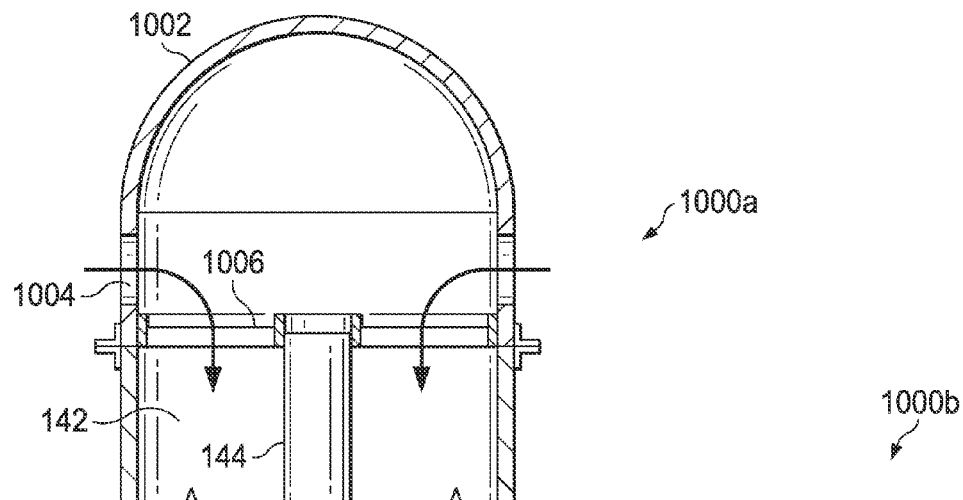
FIG. 10A is an illustration of a top module (TM) according to an implementation.
Figure 10B:
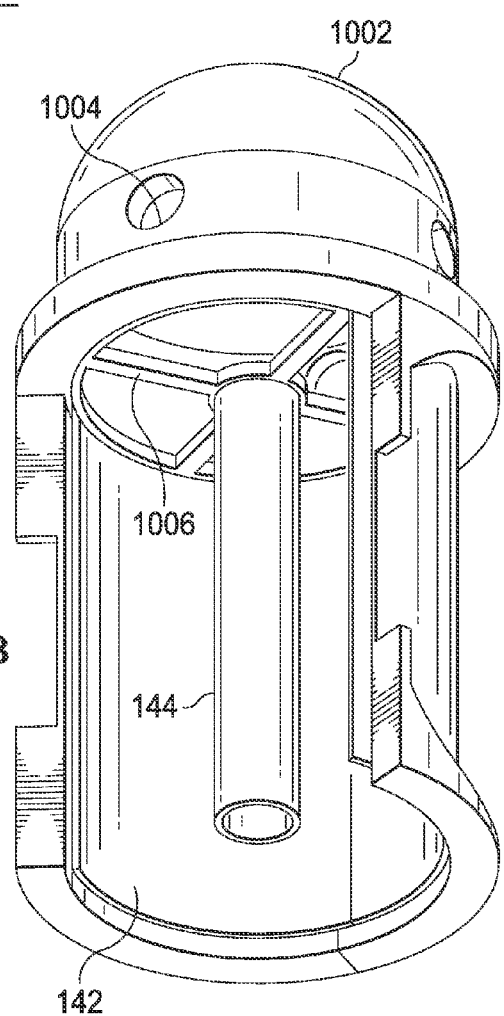
FIG. 10B is a perspective cut-away view of the illustrated TM of FIG. 10A.

FIGS. 10A and 10B illustrate views 1000a and 1000b of a TM 1002 according to an implementation. FIG. 10A is an illustration 1000a of a TM according to an implementation. The illustrated TM 1002 is round in shape with four holes 1004 where different hoses can be connected for: 1) cement 126 or fluid exit from the annulus 142, or 2) to pump cement 126 or other fluid into the annulus 142 from the top. In some implementations, a sensor 402 (not illustrated) that can measure the level of fluid inside the annulus 142 is placed on the top of the TM 1002. Wireframe 1006 can be used to provide the above-described eccentricity to the casing emulating tubing 144 if desired. In other implementations, the illustrated TM 1002 can have more or less holes 1004 in different locations on the TM 1002.

FIG. 10B is a perspective cut-away view of the illustrated TM 1002 of FIG. 10A. As can be seen in the perspective view 1000b, wireframe 1006 can be used to provide various eccentricities to the casing emulating tubing 144. Although not illustrated in FIG. 10A or 10B, in some implementations, the casing emulating tubing 144 can be sealed to prevent introduction of cement 126 or other fluid when introduced into the annulus 142.

Figure 11A:
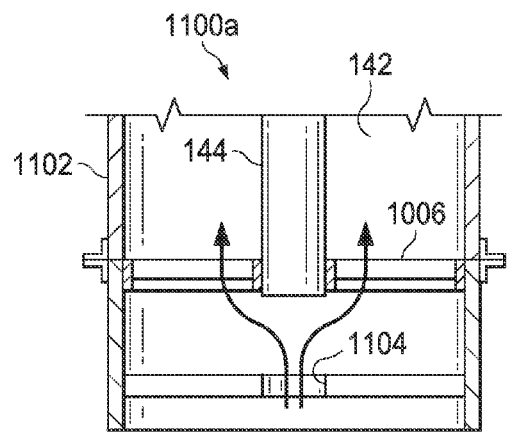
FIG. 11A is an illustration of a bottom module (BM) according to an implementation.
Figure 11B:
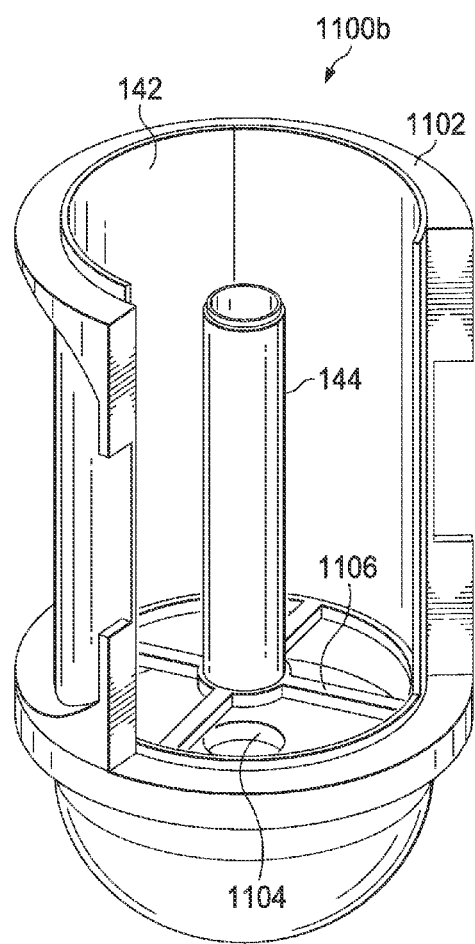
FIG. 11B is a perspective cut-away view of the illustrated BM of FIG. 11A.

FIGS. 11A and 11B illustrate views 1100a and 1100b of a bottom module according to an implementation. FIG. 11A is an illustration 100a of a BM according to an implementation. The illustrated BM 1102 is flat in shape with one hole 1104 where a hose from a cement pump can be connected to allow the injection of cement 126 or other fluids from the BM 1102. The hole 104 can also be used as a cement 126/fluid drain to remove cement 126/fluid injected from the TM 1002. In some implementations, the BM 1102 is sensed for pressure and temperature using one or more sensors 402. In addition, in some implementations, a capacitive load cell as described in FIG. 8 can be installed to measure a fluid-column weight as a function of time. In some implementations, other types of sensors can be substituted for, or used in conjunction with, the capacitive load cell to collect data. For example, other sensors could be for temperature, pressure, strain, and/or other data. In other implementations, the illustrated BM 1102 can have more or less holes 1104 in different locations on the BM 1102.

FIG. 11B is a perspective cut-away view of the illustrated BM 1102 of FIG. 11A. As can be seen in the perspective view 1100b, wireframe 1006 can be used to provide various eccentricities to the casing emulating tubing 144. Although not illustrated in FIG. 11A or 11B, in some implementations, the casing emulating tubing 144 can be sealed to prevent introduction of cement 126 or other fluid when introduced into the annulus 142.

In some implementations, an exemplary method for measuring fluid invasion and migration into a cement column is as follows. At a high-level, the MADSAW system is assembled to represent a well scenario of interest by, for example, assembling appropriate well-wall emulating modules in a particular order. A cement slurry is then placed into the annular space of the MADSAW system and relevant variables measured during cement gelation and hydration to evaluate the likelihood of fluid invasion and migration.

At a low-level, following the assembly of the MADSAW system, the first step is to prepare a cement slurry and continuously pump it from the bottom of the annulus. When a sensor placed on the top of the annulus indicates that the slurry has achieved a desired position in the annulus, the pumping is stopped and a test time is set to zero to identify the end of cement placement and the start of the test. Recording of some or all available measurements is then started. In some implementations, measurements can include temperature and pressure as a function of depth, cement slurry weight, position of the top of cement, fluid-loss rate, and or other measurement.

During the test, as the time increases and the gelation and hydration of the cement evolves, a cement volume reduction may be observed. The volume reduction is more relevant when both an early shrinkage of the cement and fluid loss are more significant. The volume reduction coupled with changes in rheology of the cement leads to a decrease in pressure inside the cement slurry column. As a consequence, two possible behaviors will likely be observed: 1) the pressure decrease is not so high that the pressure inside the cement slurry column is maintained above the outside annular pressure until the cement sets or 2) the pressure decrease is high enough to cause the pressure inside the cement slurry column to become lower than the pressure of the hermetic enclosures of FEMs.

Behavior 1) indicates little-to-no risk of fluid invasion during cement setting. Behavior 2), however, indicates a tendency of the pressurized fluid inside hermetic enclosures to invade the cement slurry column. If the fluid inside the hermetic enclosures is a gas, there is also a possibility of gas bubble migration along the cement column and trapped gas at the top of the annulus. The gas invasion and the gas migration can be detected and evaluated by the sensors along the entire length of the MADSAW.

In some implementations, five primary cement-related factors are taken into account by this method. Fluid loss is directly measured by the MADSAW system. In addition, due to the fact that there would then be a total volume reduction of the cement column, the fluid loss, weight of the cement, and cement shrinkage can be measured as a function of time. Moreover, due to fluid loss and shrinkage, the yield stress and transient rheology of the cement can affect the measured pressure inside the cement column. Finally, as actual cement is being used in the test, if the pressure decrease inside the cement column is significant, compressibility of the cement can also play a role in fluid invasion and migration measurements.

In some implementations, the MADSAW can also be used to simulate fluid displacement and/or flow inside an actual well if modifications are made or new special modules are designed. As will be appreciated by those of skill in the art, operations involving fluid displacements, circulation, or cementing can also be simulated by the MADSAW and are considered to be within the scope of this disclosure.

The foregoing description is provided in the context of one or more particular implementations. Various modifications, alterations, and permutations of the disclosed implementations can be made. Thus, the present disclosure is not intended to be limited only to the described and/or illustrated implementations, but is to be accorded the widest scope consistent with the principles and features disclosed herein.

What is claimed is:

1. A cement testing system, comprising:
an upper end module;
a lower end module;
a casing emulating tubing comprising one or more intermediate tubing modules, wherein the casing emulating tubing couples to the upper end module and to the lower end module and emulates a wellbore casing;
intermediate well-wall emulating modules that couple end-to-end and to the upper end module and the lower end module to form an annulus around the casing emulating tubing for receiving cement therein, each of the intermediate well-wall emulating modules comprising individual sidewall sections configured to be removably coupled together and each of the sidewall sections having opposing edges extending along lengths of the sidewall sections, and a flange located on the respective opposing edges of the sidewall sections that extends outwardly from and along an axial length of each of the opposing edges, the flanges configured to abut each other when the sidewall sections are joined together to form a well-wall emulating module, and
wherein a module selected from the group consisting of one or more of the intermediate well-wall emulating modules, one or more of the intermediate tubing modules, and any combination thereof comprises at least one sensor.

2. The system of claim 1, wherein the upper end module and the lower end module each comprise an internal wireframe to which the casing emulating tubing can connect, the internal wireframe configurable to put a specified eccentricity on the casing emulating tubing in relation to the outer diameter of the annulus formed by the intermediate well-wall emulating modules.

3. The system of claim 1, wherein the intermediate tubing modules that couple end-to-end and one or more of the intermediate tubing modules comprise the at least one sensor adapted to measure one or more characteristics of cement from the exterior of the casing emulating tubing.

4. The system of claim 3, wherein each intermediate tubing modules has at least one threaded end to permit two intermediate tubing modules to couple end-to-end by screwing together.

5. The system of claim 1, wherein each of the sidewall sections are curved.

6. The system of claim 1, wherein each of the sidewall sections are curved and form a portion of the complete perimeter of one of the intermediate well-wall emulating modules.

7. The system of claim 6, wherein each of the intermediate well-wall emulating modules comprises more than two curved sidewall sections, wherein each of the more than two curved sidewall sections span a same portion of the perimeter, or one or more spans a different portion of the perimeter.

8. The system of claim 6, wherein an inner surface of one of the curved sidewall sections has a specified roughness.

9. The system of claim 1, wherein one of the intermediate well-wall modules comprises a hermetic enclosure separated from the annulus by a material with a specified permeability to fluid or gas to emulate the permeability of a wall of a wellbore and a valve connected to the hermetic enclosure to establish a pressure within the hermetic enclosure.

10. The system of claim 1, wherein one of the intermediate well-wall modules comprises a one-way valve to inject a fluid or gas into the annulus.

11. A cement testing system comprising intermediate well-wall emulating modules surrounding a casing emulating tubing comprising one or more intermediate tubing modules, and forming an annulus for receiving cement therein, each of the intermediate well-wall emulating modules configured to emulate one or more different characteristics of a well wall and comprising individual sidewall sections configured to be removably coupled together and each of the sidewall sections having opposing edges extending along lengths of the sidewall sections, and a flange located on the respective opposing edges of the sidewall sections that extends outwardly from and along an axial length of each of the opposing edges, the flanges configured to abut each other when the sidewall sections are joined together to form a well-wall emulating module, and wherein a module selected from the group consisting of one or more of the intermediate well-wall emulating modules, one or more of the intermediate tubing modules, and any combination thereof comprises at least one sensor.

12. The cement testing system of claim 11, further comprising an upper end module and a lower end module that couples to the intermediate well-wall emulating modules and casing emulating tubing to seal the annulus.

13. The cement testing system of claim 11, wherein the one or more intermediate tubing modules couple end-to-end to form the casing emulating tubing.

14. The cement testing system of claim 11, wherein the intermediate well-wall emulating modules are configured to couple end-to-end.

15. A method for testing cement, comprising:
defining a casing emulating tubing by intermediate tubing modules coupled end-to-end;
forming an annulus by coupling intermediate well-wall emulating modules surrounding the casing emulating tubing together with each of the intermediate well-wall emulating modules configured to emulate one or more different characteristics of a well wall, the intermediate well-wall emulating modules comprising individual sidewall sections configured to be removably coupled together and each of the sidewall sections having opposing edges extending along lengths of the sidewall sections, and a flange located on the respective opposing edges of the sidewall sections that extends outwardly from and along an axial length of each of the opposing edges, the flanges configured to abut each other when the sidewall sections are joined together to form a well-wall emulating module;
sealing the annulus with an upper end module and a lower end module coupled to the casing emulating tubing and to the removably coupled intermediate well-wall emulating modules; and
measuring data associated with cement introduced into the annulus using at least one sensor associated with a module selected from the group consisting of one or more of the intermediate well-wall emulating modules, one or more of the intermediate tubing modules, and any combination thereof.

16. The method of claim 15, wherein cement is introduced into the annulus using the upper end module or the lower end module.

17. The method of claim 16, wherein the measured data is used to predict fluid invasion into or fluid migration through a cement column placed into the annulus of an actual well.

* * * * *